DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 30, 1971

892 O.G. 1604

T892,018

PROCESS FOR PREPARING HIGH PURITY DIHYDROISOPHORONE

William E. Wellman, 24 Cambridge Road, Edison, N.J. 08817; Paul E. Burton, 761 Austin St., Westfield, N.J. 07090; and William D. Diana, 1001 Shadow Oak Lane, Somerville, N.J. 08876

Filed Sept. 10, 1968, Ser. No. 758,839

Int. Cl. C07c *45/00, 49/30*

U.S. Cl. 260—586 R

1 Sheet Drawing. 28 Pages Specification

In the hydrogenation of isophorone to dihydroisophorone, maintaining the reaction zone at elevated pressures under mild temperature conditions significantly improves the selectivity to dihydroisophorone at high conversion levels. Isophorone is contacted with hydrogen in the presence of a hydrogenation catalyst in a hydrogenation zone wherein the hydrogen pressure in said zone is maintained between about 10 to 200 p.s.i.g. and the temperature in said zone ranges from about 25° to less than 175° C. The hydrogenation reaction product recovered from the reaction zone is distilled to obtain substantially pure dihydroisophorone. In a preferred embodiment, the hydrogenation reaction product is distilled in a first zone to separate the distillate comprising dihydroisophorone and $\beta$-isophorone from the residue comprising $\alpha$-isophorone. The distillate withdrawn from the first zone is then passed to a second zone wherein said distillate is heated at a temperature sufficient to substantially isomerize $\beta$-isophorone to $\alpha$-isophorone without causing pyrolysis of the remainder of said distillate. The effluent from said second zone is then passed to a third zone to separate the distillate comprising dihydroisophorone from the residue comprising $\alpha$-isophorone.

Nov. 30, 1971 W. E. WELLMAN ET AL T892,018
PROCESS FOR PREPARING HIGH PURITY DIHYDROISOPHORONE
Filed Sept. 10, 1968
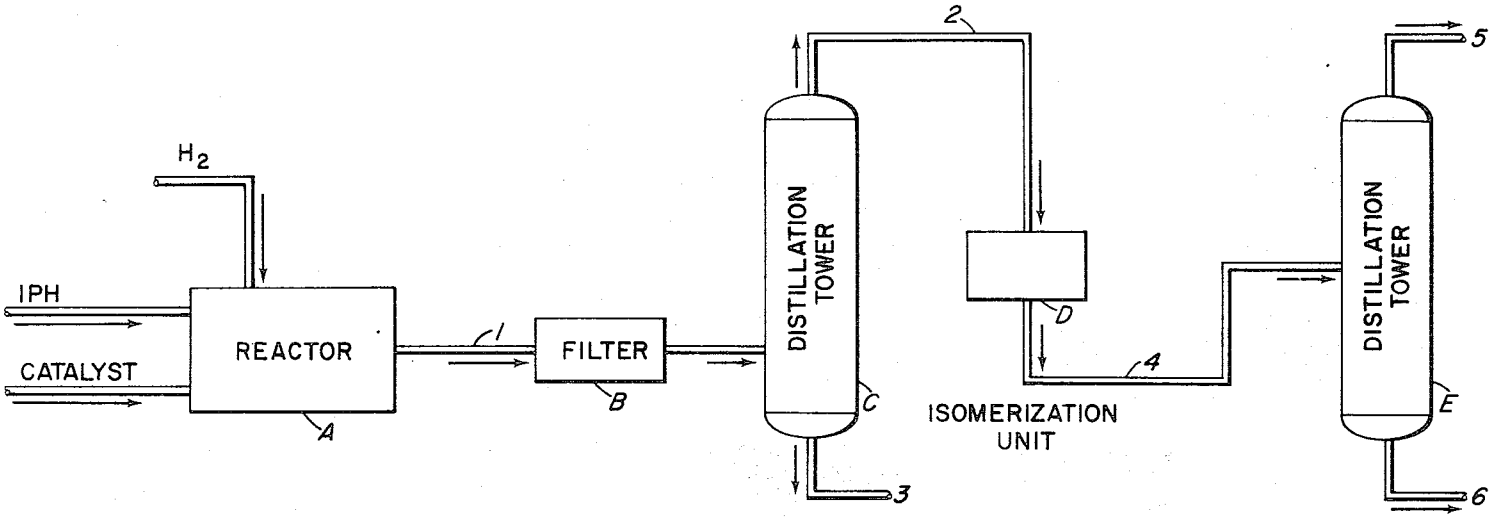
P. E. Burton
W. E. Wellman Inventors
W. D. Diana
By Attorney